Nov. 16, 1954 E. S. BOERNER Plant Pat. 1,318
ROSE PLANT
Filed Oct. 6, 1953
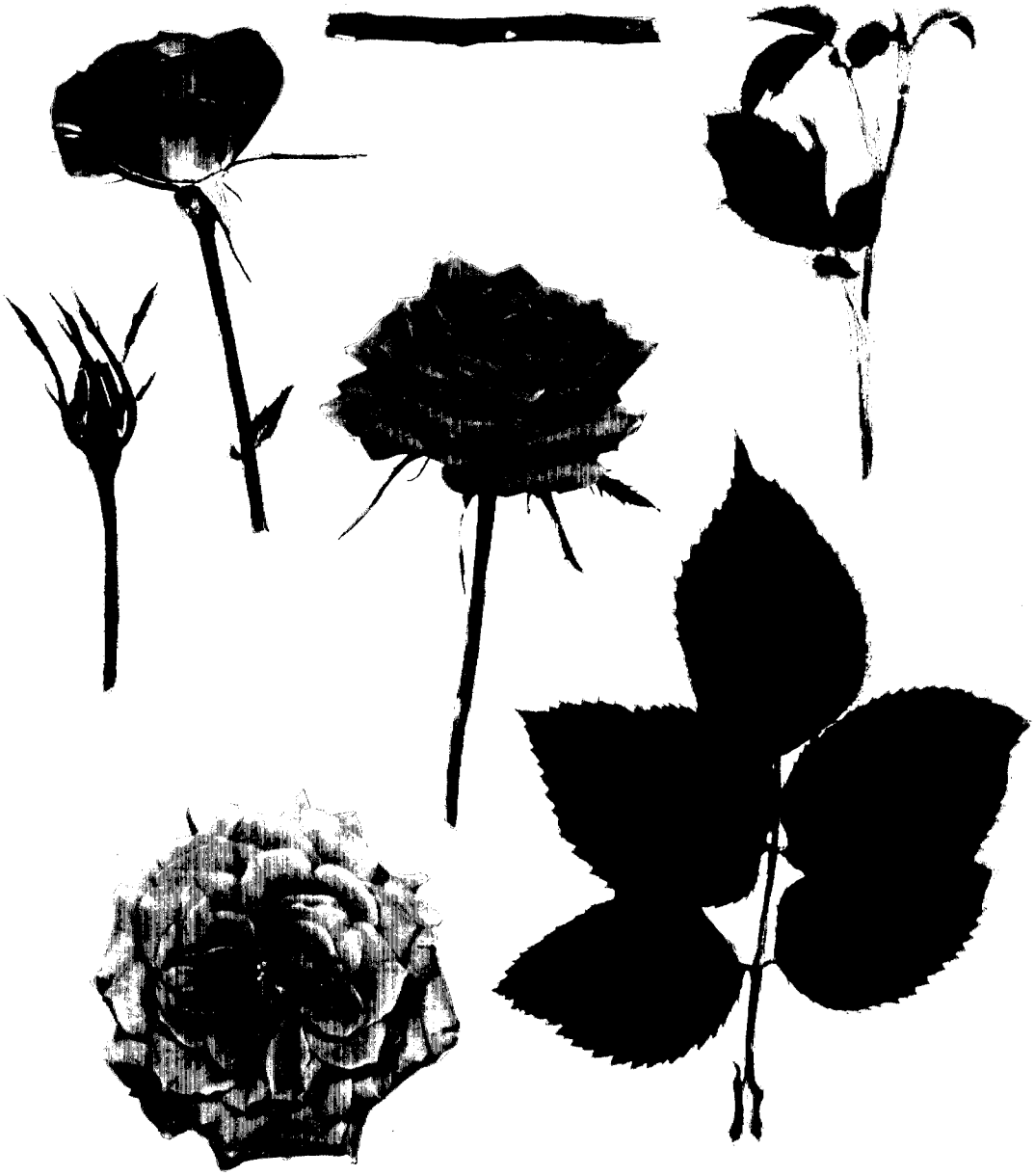
Inventor.
E. S. Boerner
By: Robb & Robb
attorneys.

United States Patent Office

Plant Pat. 1,318
Patented Nov. 16, 1954

1,318

ROSE PLANT

Eugene S. Boerner, Newark, N. Y., assignor to Jackson & Perkins Company, Newark, N. Y., a corporation of New York Application October 6, 1953, Serial No. 384,536

1 Claim. (Cl. 47—61)

The present invention relates to a new and distinct variety of rose plant of the large-flowered polyantha class, which was originated by me by crossing an unnamed and unpatented seedling of "Yellow Pinocchio" (Plant Patent No. 992) with the variety "Garnette" (unpatented).

The primary objective in making this cross was to produce a new variety of rose plant which bears blooms comparable in color and lasting quality to the blooms of the variety "Garnette," but the blooms of which new variety are larger in size than those of this parent. This objective was fully achieved, as evidenced by the fact that the blooms of the new variety average approximately 2½ to 3 inches in diameter when fully expanded, while the blooms are a velvety red (carmine) color which is retained, along with the full-petaled distinctive form of the blooms, for a period of from ten days to two weeks after cutting and when kept at ordinary room temperatures.

The foregoing characteristics and distinctions of the new variety definitely distinguish the same from the parents, as well as from all other varieties of this class, and asexual reproduction of the new variety by budding at Newark, New York, and at Pleasanton, California, shows that said characteristics and distinctions come true to form and are established and transmitted through succeeding propagations.

The accompanying illustration shows typical specimens of the flowers, foliage and stems of the new variety in various stages of development and with the colors thereof depicted as nearly true as it is reasonably possible to make the same in a color illustration of this character.

The following is a detailed description of the new variety, with color terminology in accordance with Ridgway's Color Standards and Nomenclature:

Parentage: Seedling.
- *Seed parent.*—An unnamed seedling of "Yellow Pinocchio."
- *Pollen parent.*—"Garnette."

Classification:
- *Botanic.*—Large-flowered polyantha.
- *Commercial.*—Floribunda.

FLOWER (Observations made from specimens grown at Newark, New York, in a greenhouse in the latter part of the month of May and in the early morning.)

Blooming habit: Recurrent—continuous.

Bud:
- *Size.*—Medium.
- *Form.*—Ovoid; is not affected by wet or hot weather.
- *Color.*—When sepals first divide—Oxblood Red, Plate 1. When petals begin to unfurl—Carmine, Plate 1. When half blown: inside of petals—Rose Red, Plate 12, slightly overcast with Spectrum Red, Plate 1; reverse of petals—Carmine, Plate 1, slightly overcast with Spectrum Red, Plate 1.
- *Sepals.*—Branched ("hood" above bud); curl back when petals begin to unfurl. Color: inside—Turtle Green, Plate 32; outside—Bice Green, Plate 17.
- *Calyx.*—Color—Spinach Green, Plate 5. Shape—funnel. Size—small. Aspect—smooth. Odor when rubbed—none.
- *Peduncle.* — Length — medium. Aspect — prickly. Strength—erect; slender. Color—Spinach Green, Plate 5.

- *Opening.*—Opens up well; is not affected by adverse weather conditions.

Bloom:
- *Size.*—Medium; average size when fully expanded 2½ to 3 inches.
- *Borne.*—Sometimes singly, sometimes several together and sometimes in irregular clusters.
- *Stems.*—Medium length; strong.
- *Form (when first open).*—Cupped. Permanence—Retains its form to the end, with outer petals curling back.
- *Petalage.*—Double (full but open center). Number of petals under normal conditions—35 to 40.
- *Color.*—Center of flower—Carmine, Plate 1. Outer petals—Spectrum Red, Plate 1, lightly overcast with Carmine, Plate 1. Base of petals (aiglet)—Naphthalene Yellow, Plate 16. Inside of petals—Carmine, Plate 1, overcast with Spectrum Red, Plate 1. Reverse of petals—Pomegranate Purple, Plate 12, lightly overcast with Rose Red, Plate 12. General tonality from a distance—Carmine, Plate 1, lightly overcast with Spectrum Red, Plate 1.
- *Discoloration.*—General tonality at end of first day—Carmine, Plate 1. Second day—Carmine, Plate 1, overcast with Spectrum Red, Plate 1. Third day—Spectrum Red, Plate 1, lightly overcast with Carmine, Plate 1.

Petals:
- *Texture.*—Thick; is not affected by wet or hot weather.
- *Appearance.*—Inside—velvety. Outside—satiny.
- *Form.*—Oval.
- *Arrangement.* — Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—long. As cut flower—long.

GENITAL ORGANS

Stamens, anthers: Small; few.
- *Arrangement.*—Regular around styles.
- *Color.*—Light Cadmium, Plate 4.

Stamens, filaments (threads): Short. Color—Clear Dull Green-Yellow, Plate 17.

Pollen: Color—Light Chalcedony Yellow, Plate 17.

Styles: Loosely separated; uneven length; medium length; thin.

Stigmas: Color—Chalcedony Yellow, Plate 17.

Ovaries: All enclosed in calyx.

Hips: None.

Seeds: None.

PLANT

Form: Bush.

Growth: Vigorous; upright; compact.

Foliage: 5 to 7 leaflets.
- *Size.*—Medium.
- *Quantity.*—Normal.
- *Color.*—New foliage: upper side—Madder Brown, Plate 13; under side—Oxblood Red, Plate 1. Old foliage: upper side—Varley's Green, Plate 18; under side—Cress Green, Plate 31.
- *Shape.*—Oval pointed.
- *Texture.*—Upper side—glossy. Under side—smooth.
- *Ribs and veins.*—Ordinary.
- *Edge.*—Serrated (saw-toothed).
- *Serration.*—Both double and single; small.
- *Leaf stem.*—Color—Absinthe Green, Plate 31, lightly overcast with Mikado Brown, Plate 29. Under side—prickles.
- *Stipules.*—Medium length; bearded.

Wood:
- *New wood.*—Color—Light Cress Green, Plate 31. Bark—smooth.
- *Old wood.*—Color—Light Bice Green, Plate 17. Bark—smooth.

Thorns:

*Thorns.*—Quantity: On main stalks from base—ordinary; on laterals from stalk — ordinary. Form—narrow base; medium length; hooked downward. Position—irregular. Color (when young)—Light Vinaceous Cinnamon, Plate 29.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the general similarity of the color, form and lasting quality of its blooms to those of its parent variety "Garnette," but its blooms being larger in size than those of "Garnette."

No references cited.